United States Patent [19]

Tai et al.

[11] Patent Number: 5,180,700

[45] Date of Patent: Jan. 19, 1993

[54] REGENERATION AND EXTENSION OF LIFETIME OF DEHYDROGENATION CATALYSTS USED IN THE PREPARATION OF 2-ALKYLPYRIMIDINES

[75] Inventors: Eva F. Tai; John W. Hull, Jr.; Kenneth E. First, all of Midland, Mich.

[73] Assignee: DowElanco, Indianapolis, Ind.

[21] Appl. No.: 698,872

[22] Filed: May 13, 1991

[51] Int. Cl.⁵ .................. B01J 23/96; B01J 38/14; B01J 38/18; C07D 239/26

[52] U.S. Cl. ..................... 502/50; 502/49; 502/52; 544/242; 564/159

[58] Field of Search .............. 502/52, 49, 50, 51, 502/38

[56] References Cited

U.S. PATENT DOCUMENTS

| | | | |
|---|---|---|---|
| 3,050,523 | 8/1962 | Erner et al. | 544/242 |
| 3,126,381 | 3/1964 | Langis et al. | 544/242 |
| 3,366,634 | 1/1968 | McBride, Jr. et al. | 544/242 |
| 4,376,201 | 3/1983 | Pews | 544/242 |
| 4,493,929 | 1/1985 | Pews | 544/242 |
| 4,880,929 | 11/1989 | Teunissen et al. | 544/242 |
| 4,999,427 | 3/1991 | Hull, Jr. | 544/242 |

FOREIGN PATENT DOCUMENTS

| | | |
|---|---|---|
| 205312 | 6/1955 | Australia ................... 502/49 |
| 0117882 | 9/1984 | European Pat. Off. |
| 0192297 | 8/1986 | European Pat. Off. |
| 0192299 | 8/1986 | European Pat. Off. |

OTHER PUBLICATIONS

S. R. Aspinall, J. Am. Chem. Soc. (Aug. 1940)—vol. 62 pp. 2160–2162.
M. Tsuchiya et al., Yakugaku Zasshi, vol. 96(8), pp. 1005–1012 (English translation supplied).

Primary Examiner—Paul E. Konopka
Attorney, Agent, or Firm—Craig E. Mixan; Kenneth L. Loertscher

[57] ABSTRACT

The useful life of the palladium dehydrogenation catalyst used in the preparation of 2-alkylpyrimidines from 1,3-diaminopropane and an appropriate alkanecarboxylic acid in a continuous vapor phase process is substantially increased by employing a stoichiometric excess of the carboxylic acid and by using catalyst pellets of less than 3-4 mm diameters. Additionally, the dehydrogenation catalyst can be regenerated in situ by controlled air oxidation below 350° C.

2 Claims, 1 Drawing Sheet

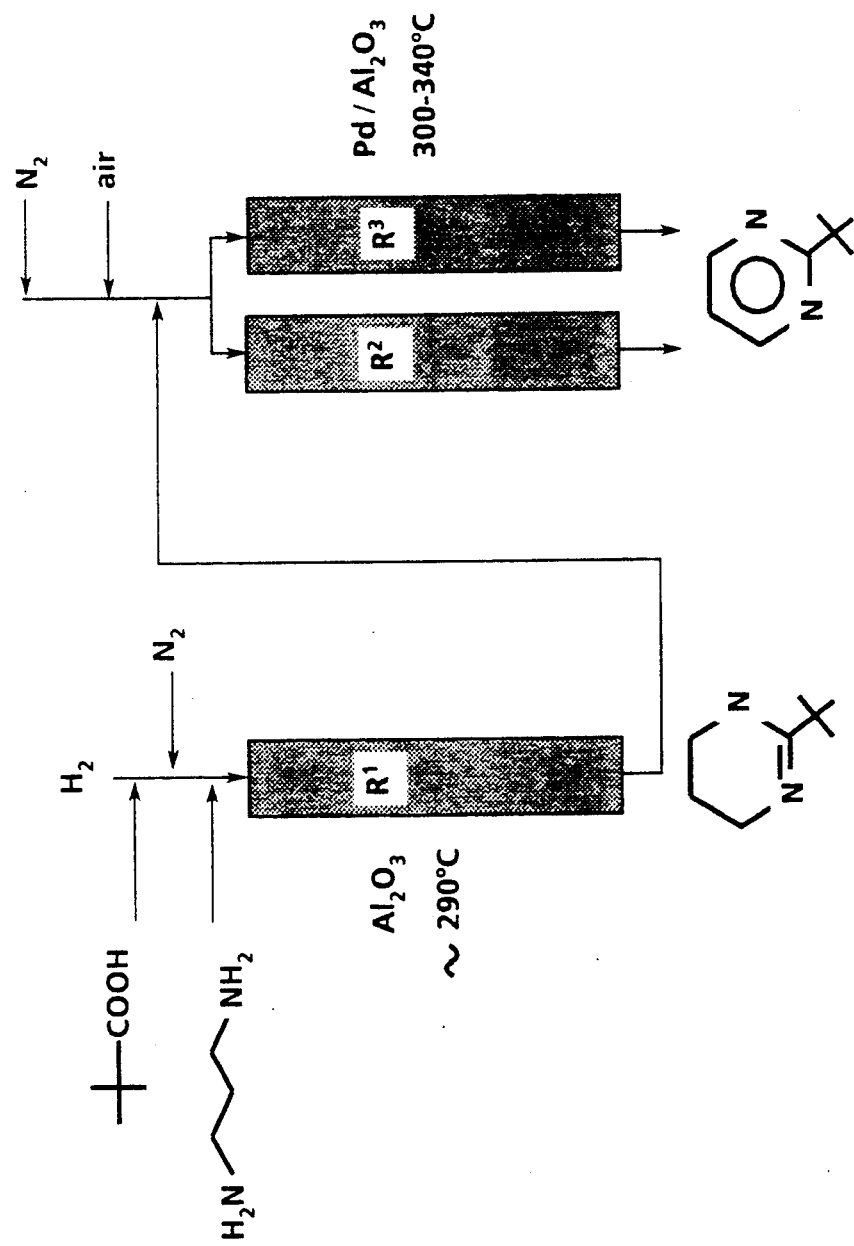

REGENERATION AND EXTENSION OF LIFETIME OF DEHYDROGENATION CATALYSTS USED IN THE PREPARATION OF 2-ALKYLPYRIMIDINES

FIELD OF INVENTION

The present invention concerns a process for regenerating and extending the lifetime of noble metal dehydrogenation catalysts used in preparing 2-alkylpyrimidines. More particularly, the present invention concerns the on-site regeneration and improved cycle lifetimes of palladium dehydrogenation catalysts used in preparing 2-alkylpyrimidines from the corresponding 2-alkyltetrahydropyrimidines.

BACKGROUND OF THE INVENTION

2-Alkylpyrimidines, particularly 2-tert-butylpyrimidine, are advantageously employed as intermediates for the preparation of certain organophosphorus insecticides as described in U.S. Pat. No. 4,127,652.

The preparation of 2-alkylpyrimidines is taught in U.S. Pat. No. 3,050,523. That process requires the reaction of an alkylene 1,3-diamine with an organic carboxylic acid, ester or amide over a supported noble metal catalyst having dehydration and dehydrogenation activity. More recently, the individual steps (a-c) of the conversion of 1,3-diaminopropane and an alkanecarboxylic acid to a 2-alkylpyrimidine have been investigated; see, for example, U.S. Pat. Nos. 4,376,201; 4,493,929; 4,880,929; and 4,999,427; and European Patent Application Publication Nos. 117,882; 192,297; and 192,299.

a) Amidation

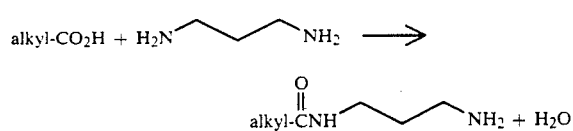

b) Cyclization/Dehydration

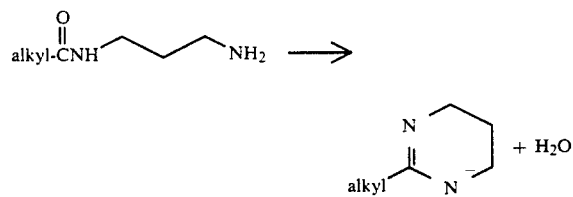

c) Dehydrogenation

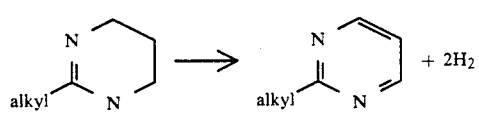

U.S. Pat. No. 4,376,201 describes the vapor phase reaction wherein a 3-aminopropyl carboxylic acid amide is cyclized and dehydrogenated over a supported platinum or palladium catalyst (steps b+c).

U.S. Pat. No. 4,493,929 describes the separation of steps b+c and the improved vapor phase reaction wherein 2-alkylpyrimidines are obtained in high yield and purity by the dehydrogenation of a 2-alkyltetrahydropyrimidine under conditions which do not generate water and in which no water is added (step c).

European Patent Application Publication No. 117,882 describes an overall process for the preparation of 2-tert-butylpyrimidine which comprises the following individual steps: a) the preparation of 3-aminopropyl pivalamide by reaction of pivalic acid and an excess of 1,3-diaminopropane; b) removal of unreacted 1,3-diaminopropane by distillation and dehydration of the 3-aminopropyl pivalamide to 2-tert-butyl-1,4,5,6-tetrahydropyrimidine in the liquid phase, preferably in the presence of a solvent capable of azeotroping water; and c) the dehydrogenation of 2-tert-butyltetrahydropyrimidine to 2-tert-butylpyrimidine, under conditions in which water is neither generated nor added, over a supported noble metal catalyst.

European Patent Application Publication No. 192,297 describes the vapor phase dehydrogenation of 2-propyl- or 2-butyl-1,4,5,6-tetrahydropyrimidine over a palladium-containing catalyst in which the catalyst lifetime is prolonged by operating the presence of carbon monoxide and hydrogen (step c).

European Patent Application Publication No. 192,299 describes the multistep preparation of 2-methyl and 2-ethylpyrimidine by: the reaction of an acetic or propionic acid derivative with 1,3-diaminopropane in the liquid phase to form a 1-amino-3-amidopropane (step a); optional cyclization to the 2-methyl- and 2-ethyltetrahydropyrimidine (step b); and optional cyclization and gas phase dehydrogenation to 2-methyl- and 2-ethylpyrimidine with a palladium-containing catalyst in the presence of carbon monoxide and hydrogen (step c or steps b+c).

U.S. Pat. No. 4,880,929 describes an improved stepwise, continuous process for the preparation of a 2-alkylpyrimidine from the appropriate alkanecarboxylic acid and a 1.5 to 2.5 fold excess of 1,3-diaminopropane. In a very similar process, U.S. Pat. No. 4,999,427 describes preferred ratios of diamine to alkanecarboxylic acid of 1.1:1 to 6:1. In addition, this latter patent suggests that unreacted alkanecarboxylic acid has a deleterious effect on the lifetime of the palladium-containing dehydrogenation catalyst.

With time, the dehydrogenation catalysts typically lose their efficiency and must be replaced or regenerated Because supported palladium catalysts are prone to sintering, they are often regenerated off-site and the palladium must be reprocessed. Off-site regeneration means the undesirable shutdown of the process followed by cooling and down-loading of the catalyst. Therefore, it is highly desirable to increase the effective lifetime of the catalyst in order to extend the time between catalyst regenerations. It is also desirable to have an on-line or on-site regeneration process to minimize disruption of the operation.

SUMMARY OF THE INVENTION

One aspect of the present invention concerns an improved process for extending the lifetime of the palladium dehydrogenation catalyst used in the continuous stepwise preparation of 2-alkylpyrimidines in which 1,3-diaminopropane and an alkanecarboxylic acid are reacted in the gas phase over a metal oxide catalyst to prepare a 2-alkyl-1,4,5,6-tetrahydropyrimidine which is subsequently dehydrogenated to the 2-alkylpyrimidine over a palladium catalyst, the improvement comprising reacting the 1,3-diaminopropane and the alkanecarboxylic acid in a molar ratio of from 0.8:1 to 1:1.

Another aspect of the present invention concerns a process for extending the lifetime of the palladium dehydrogenation catalyst used in the improved process employing an excess of alkanecarboxylic acid which comprises using a catalyst having a grain size of less than 3-4 millimeters (mm).

Yet another aspect of the present invention concerns a process for the regeneration of the palladium catalyst used in the dehydrogenation of a 2-alkyl-1,4,5,6-tetrahydropyrimidine to a 2-alkylpyrimidine which comprises contacting the catalyst first with from 0.01 to 1.0 percent and then with increasing concentrations of oxygen in an inert carrier gas while controlling the temperature from between 200° and 350° C.

Thus, the present invention effectively increases the life of the catalyst and allows for the catalyst to be regenerated in situ.

BRIEF DESCRIPTION OF THE FIGURE

FIG. 1 schematically illustrates a continuous vapor phase process for the preparation of 2-tert-butylpyrimidine from 1,3-diaminopropane and pivalic acid. $R^1$ is a vertical tubular reactor in which most of the 1,3-diaminopropane and pivalic acid are condensed and cyclized to the 2-alkyltetrahydropyrimidine. $R^2$ and $R^3$ are vertical tubular reactors in which the 2-alkyltetrahydropyrimidine is dehydrogenated over a palladium catalyst to the 2-alkylpyrimidine. With parallel reactors $R^2$ and $R^3$, one reactor can be in operation while the other is being regenerated.

DETAILED DESCRIPTION OF THE INVENTION

As used herein the terms "alkane" and "alkyl" refer to a straight-chained or branched hydrocarbon group of 1 to 4 carbon atoms inclusive. Branched alkyl groups of 3 to 4 carbon atoms are preferred. Iso-propyl and tert-butyl groups are most preferred.

The vapor phase process for the preparation of a 2-alkylpyrimidine directly from 1,3-diaminopropane and an alkanecarboxylic acid in a dual catalyst system which comprises contacting 1,3-diaminopropane and the alkanecarboxylic acid in the vapor phase over a dehydration catalyst and subsequently passing the resultant stream in the vapor phase over dehydrogenation catalyst is described in U.S. Pat. Nos. 4,880,929 and 4,999,427. The preferred dehydration catalysts are silica and alumina. The preferred dehydrogenation catalysts are palladium supported, for example, on alumina.

The sequential (a) amidation, (b) cyclization/dehydration and (c) dehydrogenation reactions may typically be carried out like other vapor phase reactions in which the reactants and an appropriate diluent are mixed and passed over the catalyst at a contact time and temperature sufficient to achieve the desired conversion. Typically, a gaseous diluent, such as, for example, nitrogen or hydrogen, is employed. Hydrogen is the most preferred diluent in terms of extending the lifetime of the dehydrogenation catalyst. The mole ratio of diluent to starting material can be from about 1:1 to about 50:1. Approximately 2 to 5 moles of diluent per mole of reactant are preferred. The reaction is best conducted without a solvent, but solvents capable of dissolving the salt of the alkanecarboxylic acid and 1,3-diaminopropane, such as water or methanol, may be optionally employed.

Although the exact residence time is not critical, in order to prevent unnecessary degradation the reactants should not be permitted to remain in contact with the catalyst for a prolonged period. The preferred contact period or residence time, which depends on several factors including the temperature within the operable ranges of temperature for a particular product, is readily determined by routine experimentation. For the initial stage, the amidation and the cyclization/dehydration over the dehydration catalyst can be conducted in the range of about 220 to about 300° C., preferably from about 250 to about 290° C. The subsequent dehydrogenation over the supported palladium catalyst can be conducted in the range from about 280 to about 400° C., preferably from about 300 to about 340° C.

Operating pressures are not critical and may vary from subatmospheric to somewhat superatmospheric. Atmospheric pressure is satisfactory and is preferred.

The use of excess alkanecarboxylic acid has been found to increase the lifetime of the palladium dehydrogenation catalyst used in the conversion of the 2-alkyltetrahydropyrimidine to the 2-alkylpyrimidine. Thus molar ratios of from 0.80:1 to 1:1 of 1,3-diaminopropane to alkanecarboxylic acid are preferred.

The dehydrogenation catalyst, consisting essentially of 0.5 to 10 percent palladium supported on alumina, is typically used in the form of extruded pellets. By using pellets with a diameter of 0.5 to 2 mm as opposed to larger diameters, catalyst lifetime is substantially improved.

A vapor phase reaction system for the continuous production of 2-tert-butylpyrimidine from 1,3-diaminopropane and pivalic acid is illustrated in FIG. 1. In a typical reaction, 1,3-diaminopropane and an excess of pivalic acid, either in an aqueous solution or separately using no solvent, are passed in the presence of hydrogen over an alumina bed at about 290° C. at atmospheric pressure. The resulting vapors are passed over a bed of pelletized 1 percent palladium on alumina catalyst, having a pellet diameter of 0.5 to 2 mm, at 300 to 340° C. The vapors can be condensed and purified by distillation.

The regeneration of the palladium dehydrogenation catalyst is accomplished by the controlled oxidation of the spent catalyst at a temperature below 350° C. The catalyst is contacted first with dilute concentrations of oxygen in admixture with an inert gas such as nitrogen, and then with increasing concentrations of oxygen while controlling the temperature between 200° and 350° C. The initial dilute concentrations of oxygen, usually from about 0.01 to 1.0 percent oxygen, in an inert carrier gas are conveniently provided by mixing the appropriate amount of air with a stream of nitrogen. Not only does the nitrogen serve as a diluent for the air but, by using cool nitrogen, it also serves as a coolant to control the temperature of the exothermic reaction between the catalyst and the oxygen.

In a typical regeneration procedure, a mixture of air and nitrogen, such that the concentration of oxygen is about 0.3 percent, is passed over the catalyst bed until the initial exotherm dissipates. The temperature is controlled below 350° C. primarily by the flow of the large volume of nitrogen. Afterwards, the concentration of oxygen is gradually increased until no significant exotherm is observed. Catalyst regenerated in this manner exhibits activity approaching that of fresh catalyst.

The present invention is illustrated by the following examples: however, the examples should not be interpreted as a limitation upon the scope of the present invention.

EXAMPLE 1

1,3-Diaminopropane (DAP) and liquid pivalic acid (PA) were preheated to 290° C. and fed to a vertical tubular reactor ($R^1$: 1.5 inch diameter, 48 inch length) filled with 800 milliliters (ml) of alumina catalyst (grain size: 1-4 mm diameter). The reactor was kept at 290° C. The PA feed rate was 160 g/hour (hr), the DAP feed rate was 132 g/hr. This gave a DAP/PA molar ratio of 1.14. A mixture of 300 ml/minute (min) hydrogen and 150 ml/min nitrogen was used as the sweeping gas.

The $R^1$ reactor outlet was directly connected to the following dehydrogenation reactors $R^2$ and $R^3$. $R^2$ and $R^3$ were two vertical tubular reactors (1 inch diameter, 30 inch length) in parallel; each was filled with 250 ml of 1 percent palladium on alumina catalyst (egg-shell type catalyst, pellet diameter $\frac{1}{8}$ inch (3.17 mm)). Both dehydrogenation reactors were kept at 300° C.

The 2-tert-butylpyrimidine (TBP) product stream was condensed (20° C.) and collected. Mass recovery was calculated over a period of time as the weight ratio between the product collected and the total feed (PA+DAP). Gas chromatography (GC) was used for the determination of weight percent TBP and weight percent of 2-alkyltetrahydropyrimidine (THP) in the product. As the Pd/alumina catalyst deactivated, the THP level in the product started to increase. When the THP level reached around 2 percent, the feeds were stopped and regeneration of the Pd/Alumina catalyst was started as follows:

$R^2$ and $R^3$ were kept at 300° C. while being disconnected from $R^1$. The nitrogen and air lines were then connected to each dehydrogenation reactor. A nitrogen flow of 8,000 ml/min and an air flow of 150 ml/min was used to initiate the oxidation. This gave an overall oxygen concentration of 0.3 percent. A set of combustion exotherms of 10°-20° C. moving as waves down the catalyst bed was obtained. The duration of the initial combustion was about four hr. Afterwards, cutting the nitrogen flow down to 4,000 ml/min but leaving the air flow at 150 ml/min (0.6 percent oxygen), a second set of exotherms similar to those of the first combustion was obtained. The air flow was then increased to 4,000 ml/min while maintaining the nitrogen flow at 400 ml/min (oxygen concentration of 10 percent), yet no significant exotherm was observed. The nitrogen flow was then totally stopped, leaving 4,000 ml/min of air to finish the oxidation at 300° C. for overnight. The regeneration was completed.

The air oxidized Pd/alumina beds were purged with nitrogen, followed by a reduction with hydrogen. The regenerated catalyst beds were reconnected to $R^1$ and the PA and DAP feeds were started.

The performance of the Pd/alumina catalyst in the dehydrogenation of THP to TBP can be represented by:

a. the averaged weight percent TBP in the product collected; this represents the selectivity,
b. the averaged percent molar yield based on PA and DAP; this represents the mass recovery,
c. the total run time obtained before the 2-3 percent THP cut-off was reached; this represents the lifetime in terms of process time, and
d. the life-time in terms of the total amount of TBP collected in a run divided by the amount of catalyst used, in #TBP/#catalyst: this represents the total activity in the catalyst.

Table 1 lists the performance results of the fresh and the regenerated Pd/alumina catalyst used in Example 1.

TABLE 1

CATALYST REGENERATION RESULTS

| Performance character | $R^2$ Reactor | | | | $R^3$ Reactor | | | |
|---|---|---|---|---|---|---|---|---|
| | fresh | 1st | 2nd | 3rd | fresh | 1st | 2nd | 3rd |
| wt % TBP | 54 | 53 | 52 | 50 | 54 | 54 | 52 | 50 |
| % yield, PA | 62 | 61 | 60 | 58 | 62 | 62 | 60 | 58 |
| % yield, DAP | 54 | 54 | 53 | 51 | 54 | 54 | 53 | 51 |
| run-time (hr) | 100 | 100 | 100 | 100 | 100 | 100 | 100 | 100 |
| # TBP/# catalyst | 28 | 28 | 26 | 25 | 28 | 28 | 26 | 25 |

EXAMPLE 2

In the manner described in Example 1, the dehydrogenation was carried out with $R^2$ at 320° C. and $R^3$ at 340° C. The feed rates were 156 g/hr PA and 124 g/hr DAP; the DAP/PA molar ratio was still in the range of 1.1:1. The same regeneration recipe was used as in Example 1, except that the regeneration temperature was 320° C. instead of 300° C. The results are listed in Table 2.

TABLE 2

CATALYST REGENERATION RESULTS

| Performance character | $R^2$ fresh | (320° C.) 1st regen. | $R^3$ fresh | (340° C.) 1st regen.* |
|---|---|---|---|---|
| wt % TBP | 57 | 56 | 60 | 59 |
| % yield, PA | 65 | 64 | 69 | 68 |
| % yield, DAP | 59 | 58 | 63 | 62 |
| run-time (hr) | 72 | 71 | 38 | 33 |
| # TBP/# catalyst | 20 | 20 | 11 | 9 |

*The run was made at 330° C. instead of 340° C. after the regeneration.

EXAMPLE 3

In the same manner described in Example 1, the dehydrogenation was carried out with excess PA and with $R^2$ and $R^3$ initially at 320° C., followed by a temperature ramp to 340° C. The fresh catalyst in $R^2$ was prewashed with steam (at 25 psi), but the $R^3$ side was not. The feed rate was 130 g/hr PA and 80 g/hr DAP; the DAP/PA molar ratio was in the range of 0.85:1. The results are listed in Table 3.

TABLE 3

CATALYST LIFETIME AND REGENERATION RESULTS

| Performance character | $R^2$ Reactor | | $R^3$ Reactor | |
|---|---|---|---|---|
| | fresh 320/340* | 1st regen. 320/340** | fresh 320/340* | 1st regen. 320/340** |
| wt % TBP | 52/52 | 52/52 | 53/52 | 53/52 |
| % yield, PA | 57/57 | 57/57 | 58/57 | 58/57 |
| % yield, DAP | 66/66 | 66/66 | 67/66 | 67/66 |
| run-time (hr) | 150/245 | 148/224 | 150/245 | 148/224 |
| # TBP/# catalyst | 31/53 | 31/50 | 31/52 | 31/48 |

*Temperature was ramped from 320° C. to 340° C. from 150 to 245 hr.
**Temperature was ramped from 320° C. to 340° C. from 148 to 224 hr during run on the regenerated catalyst.

EXAMPLE 4

In the manner described in Example 1, the dehydrogenation was carried out with different space velocities by packing $R^3$ with only 125 ml fresh catalyst, the remainder of the reactor being filled with inert Quartz packing. The feed rate was 166 g/hr PA and 103 g/hr DAP: the DAP/PA molar ratio was in the range of 0.85:1. Both $R^2$ and $R^3$ were kept at 340° C. The results are shown in Table 4. The different packing in the catalyst beds caused 30 percent more product to be collected in the $R^3$ side. Based on this, the reported space velocity (SV) was calculated as 0.47 g starting material per milliliter of catalyst (bulk volume) per hour for $R^2$, and that of 1.22 for $R^3$.

TABLE 4

| CATALYST LIFETIME RESULTS | | |
|---|---|---|
| Performance character | $R^2$ Reactor (SV = 0.47)* | $R^3$ Reactor (SV = 1.22)* |
| wt % TBP | 56 | 53 |
| % yield, PA | 62 | 58 |
| % yield, DAP | 73 | 68 |
| run-time (hr) | 80 | 13 |
| # TBP/# catalyst | 20 | 8 |

*Space velocity is the total feed of the starting material (PA and DAP) divided by the bulk volume of the catalyst in the reactor. it therefore has the unit of g/ml-catalyst/hr.

EXAMPLE 5

In the manner described in Example 1, an experiment with different diameter catalyst was carried out. The catalyst was 1 percent Pd/Alumina in an egg-shell configuration, but of 1/16 inch (1.59 mm) diameter. The PA feed rate 165 g/hr and the DAP feed rate was 102 g/hr. This again gave an excess PA condition with a DAP/PA molar ratio of 0.85. $R^2$ was kept at 340° C., while $R^3$ was kept at 320° C. The results are listed in Table 5.

TABLE 5

| CATALYST LIFETIME RESULTS | | |
|---|---|---|
| Performance character | $R^2$ (340° C.) (SV = 0.49)* | $R^3$ (320° C.) (SV = 0.58)* |
| wt % TBP | 56 | 54 |
| % yield, PA | 62 | 60 |
| % yield, DAP | 73 | 70 |
| run-time (hr) | 555 | 555 |
| # TBP/# catalyst | 167 | 188 |

*Space velocity in terms of the total grams of the starting material (PA + DAP) per millimeter of the catalyst (bulk volume) per hr.

What is claimed is:

1. A process for the regeneration of the palladium catalyst used in the dehydrogenation of a 2-alkyl-1,4,5,6-tetrahydropyrimidine to a 2-alkylpyrimidine consisting essentially of: (a) contacting the catalyst first with from 0.01 to 1.0 percent oxygen in an inert carrier gas until the initial exotherm dissipates and then with increasing concentrations of oxygen in an inert carrier gas until no significant exotherm is any longer observed, all the while controlling the temperature between 200 and 350° C.; (b) purging the catalyst with nitrogen; and (c) reducing the catalyst with hydrogen.

2. The process of claim 1 in which the gas stream comprised of oxygen in the inert carrier gas is provided by mixing the appropriate amount of air with a stream of nitrogen.

* * * * *